(12) United States Patent
Roques

(10) Patent No.: US 7,230,147 B2
(45) Date of Patent: Jun. 12, 2007

(54) PROCESS FOR FUNCTIONALIZING A DOUBLE BOND

(75) Inventor: Nicolas Roques, Lyons (FR)

(73) Assignee: Shasun Pharma Solutions Limited, Cranbury, NJ (US)

( * ) Notice: Subject to any disclaimer, the term of this patent is extended or adjusted under 35 U.S.C. 154(b) by 24 days.

(21) Appl. No.: 10/866,586

(22) Filed: Jun. 11, 2004

(65) Prior Publication Data
US 2004/0225160 A1 Nov. 11, 2004

Related U.S. Application Data

(63) Continuation of application No. 10/203,075, filed on Aug. 6, 2002, now abandoned.

(30) Foreign Application Priority Data
Feb. 11, 2000 (FR) .................................. 00 01744

(51) Int. Cl.
C07C 17/04 (2006.01)
C07C 41/05 (2006.01)
C07C 41/06 (2006.01)

(52) U.S. Cl. ...................... 570/172; 570/171; 570/123; 570/142; 570/162; 568/683; 568/684; 568/681; 560/240; 560/229; 556/476

(58) Field of Classification Search ................ 570/172, 570/171, 123, 142, 162; 568/683, 684, 681; 560/240, 229; 556/476
See application file for complete search history.

(56) References Cited

U.S. PATENT DOCUMENTS 5,773,538 A * 6/1998 Feiring ........................ 526/146

FOREIGN PATENT DOCUMENTS

DE 849061 9/1960
DE 904263 8/1962

OTHER PUBLICATIONS

N. Kamigata: "Novel perfluoroalkylation of alkenes with perfluoroalkanesulphonyl chlorides catalysed by a ruthenenium(II) complex"—Journal of the Chemical Society, Perkin Transactions 1, 1991, pp. 627-633, XP002151394, Letchworth GB, p. 629, table 4.
W-Y Huang: "Reactions of perfluoroalkanesulfonyl bromide" Bulletin De La Societe Chimique De France, No. 6, 1986, pp. 881-884, XP000938552, Paris, FR.

* cited by examiner

*Primary Examiner*—Elvis O. Price
(74) *Attorney, Agent, or Firm*—B. Aaron Schulman; Stites & Harbison PLLC

(57) ABSTRACT

The invention concerns a method for functionalizing a double bond and, more particularly, a double bond bearing a metalloid atom. Said functionalization is produced by the action of perhalogenated sulphonyl chloride on the carbon bearing sulphur in the presence of a free radical initiator, preferably by homolytic cleavage. The invention is useful in organic synthesis.

8 Claims, No Drawings

PROCESS FOR FUNCTIONALIZING A DOUBLE BOND

This application is a continuation of U.S. application Ser. No. 10/203,075, filed on Aug. 6, 2002 now abandoned.

The present invention relates to a process for functionalizing a double bond, and more particularly a double bond bearing a metalloid atom. More particularly, the present invention is directed toward adding to a double bond, on the one hand, and to one of the atoms a halogen atom and, on the other hand, to the other carbon-based radical whose carbon atom is perhalogenated.

Compounds comprising perhalogenated and especially perfluoro carbon atoms play an increasingly important role in derivatives with biological activity, whether this biological activity is exerted in the animal kingdom or in the plant kingdom.

The synthesis or grafting of these perhalogenated and more preferentially perfluoro compounds is often difficult and requires expensive means.

Among the techniques that have been proposed is the one consisting in subjecting a double bond to the action of a sulfonyl halide. In particular, the action of trifluoromethanesulfonyl bromide has already been described in the Bulletin de la Société Chimique de France, No. 6, 1986, from page 881 to page 884.

However, sulfonyl bromide is difficult and expensive to handle, especially on account of the high instability of this bromide. In addition, the bromide, like the chloride, is a powerful oxidizing agent which can modify the capacities for survival of the products obtained during this addition. The bromide ions formed during the reaction that react with the residual bromide can lead to bromine, which is then a source of further spurious reactions.

Trifluoromethanesulfonyl chloride, which is occasionally known as triflyl chloride, is significantly less reactive than the bromide; thus, it has been attempted to use very specific ruthenium complexes (Ru(P☐$_3$)Cl$_2$) to catalyze the addition to double bonds.

This addition appears to be relatively versatile, but the reactions are often difficult to reproduce and the results appear to be somewhat erratic.

It has also been proposed, in the case of double bonds bearing a silicon atom, to use free-radical generators such as tert-butyl peroxide.

One of the major risks of this technique lies in the fact that double bonds, under the action of free radicals, have a tendency to polymerize and not to lead to the addition reaction. Another risk is an oxidation with a chlorine according to a mechanism of positive chlorine type.

Thus, in the course of the study that led to the present invention, it has been possible to show that the action of sulfonyl chlorides on double bonds activated with an aromatic nucleus leads essentially to polymerization reactions rather than addition reactions.

In addition, certain double bonds, especially those that present major advantages for manufacturing synthons, are often not reactive enough to form the desired addition compounds.

It is thus seen that the decomposition of sulfonyl chlorides that are perhalogenated on the sulfur-bearing carbon of the sulfonyl bonds does not give an addition reaction on a double bond with good results, except in an extremely limited number of already-functionalized products.

Accordingly, one of the aims of the present invention is to define a family of compounds bearing already-functionalized double bonds, that can give acceptable addition yields with a technique of decomposition of sulfonyl chloride initiated by free radicals.

Another aim of the present invention is to provide an optimization of the operating conditions for this novel family of compounds.

Another aim of the present invention is to provide a process that does not require expensive catalysts such as those based on metals from column VIII, especially of the platinum mine, and in particular ruthenium.

Another aim of the present invention is to provide a process in which ruthenium, especially in the form coordinated with phosphines and especially aromatic phosphines, is present in an amount such that the [Ru]/[sulfonyl chloride perhalogenated on the sulfur-bearing carbon] molar ratio is not more than 1%, advantageously 0.1% and preferably 0.01%. It is even preferable for it not to be present.

Another aim of the present invention is to provide a process in which the platinum mine metals are present in an amount such that the [sum of the platinum mine metals]/ [sulfonyl chloride perhalogenated on the sulfur-bearing carbon] molar ratio is not more than 1%, advantageously 0.1% and preferably 0.01%. It is even preferable that they are not present.

Another aim of the present invention is to provide a process in which the metals from column VIII are present in an amount such that the [sum of the metals from column VIII]/[sulfonyl chloride perhalogenated on the sulfur-bearing carbon] molar ratio is not more than 1%, advantageously 0.1% and preferably 0.01%. It is even preferable for them not to be present.

Another aim of the present invention is to provide novel intermediates allowing novel synthetic routes.

The Periodic Table of the Elements used in the present patent application is that of the supplement to the Bulletin de la Société Chimique de France, January 1966, No. 1.

It may be useful to recall that the expression "identical or different" is used to indicate that the substituents under consideration may or may not be the same.

These aims and others which will become apparent hereinbelow are achieved by means of a process for functionalizing a double bond corresponding to formula I:

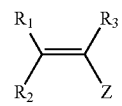

in which $R_1$, $R_2$ and $R_3$, which may be identical or different, are chosen from hydrogen and hydrocarbyls attached to said double bond via a carbon of sp$^3$ hybridization;
in which Z is chosen from:
  halogens, advantageously chlorine and fluorine;
  residues such that ZH is an oxygenated acid;
  radicals of formula (CHR')$_m$-Ξ with Ξ chosen from halogens;
  and radicals of formula (CHR')$_m$—Y(O)$_q$—R$_4$ in which
    Y is a chalcogen, advantageously a light chalcogen;
    q is zero or an integer not more than 3, advantageously not more than 2 and preferably not more than 1, with the condition that when Y is oxygen, q is equal to zero;
    R' represents a hydrocarbyl, advantageously of not more than four carbons, or preferably a hydrogen;
    m is equal to 1 or preferably to zero;

and $R_4$ is chosen from a hydrocarbyl or silyl group;
by the action of sulfonyl chloride perhalogenated on the sulfur-bearing carbon (of the sulfonyl function) in the presence of a free-radical initiator, preferably by homolytic cleavage.

The expression "perhalogenated carbon" should be understood as meaning a carbon of $sp^3$ nature optionally substituted with not more than two, and advantageously not more than one, electron-withdrawing group(s), and bearing no hydrogen, all the other atoms being halogens. It is preferable for these halogens borne by said perhalogenated carbon all to be chlorine or fluorine and preferably all fluorine.

It is important that the radicals $R_1$, $R_3$ and $R_2$, when they are hydrocarbyls (i.e. comprising hydrogen and carbon, but possibly comprising other atoms), are attached to the double bond via one of their $sp^3$ carbons, otherwise the reactivity toward the sulfonyl chloride is greatly affected thereby. In particular, the presence of an aromatic directly attached to the double bond plays an extremely unfavorable role. It is also recommended to avoid carbon atoms that are both allylic and benzylic. More generally, even when they are not conjugated with said double bond, the presence of an aromatic in the molecule is unfavorable. Thus, the presence of an aromatic in Z, especially when ZH is an oxygenated acid, is unfavorable especially when an aromatic nucleus is separated from a carbon of said double bond by less than two atoms of $sp^3$ hybridization (oxygen or carbon, preferably at least two $sp^3$ carbons). It should be noted that there is overlap between the definition of Z, $Z=(CHR')_m-Y(O)_q-R_4$ and that which indicates that Z is such that ZH is an oxygenated acid, especially when m is equal to zero, when q is equal to zero, when Y is oxygen and $R_4$ is a hydrocarbon radical attached to Y via an electron-withdrawing function such as, especially, carbonyl (—CO—), carbonate (—CO—O—), sulfonyl ($SO_2$), sulfoxide (—SO—), sulfate (—$SO_3$—), phosphate [P(=O)(—O—)O—], phosphonate [P(=O)(—O—)—] and phosphinate [P(=O)(—)—].

For reasons of steric bulk, it is recommended to choose the radicals $R_1$, $R_3$ and $R_2$ such that at least one and preferably two of these three radicals is hydrogen. It is also preferable that neither $R_1$ nor $R_2$ is tertiary. It is also preferable that at least one, and even both, of the radicals $R_1$ and $R_2$ are hydrogen.

It is preferable that the initiator generating the free radicals releases these radicals after a homolytic cleavage, i.e. a cleavage taking place between two atoms of the same element and generating an electron radical on each of the two atoms. This cleavage may be actinic, catalytic or, preferably, thermal.

The cleavage may also be heterolytic when systems are used involving metals that have two valency states (iron or copper) with peroxides and especially hydroperoxides.

Examples of preferred initiators that should be mentioned include various peroxides, preferably symmetrical, and various azo compounds, such as azobisisobutyronitrile (reference may be made especially to the "Polymer Handbook"). Among the peroxides, mention may be made of alkyl peroxides and especially tert-alkyl peroxides, and acyl peroxides, especially alkanoyl peroxides, that are preferably symmetrical.

The acyl peroxides that may be used are preferably peroxides whose acyls are of low molecular weight, i.e. their carbon number is not more than 10, and preferably not more than 6 when they are aliphatic, but it is preferable to use acyl peroxides of aromatic nature, for instance benzoyl peroxide.

The free-radical initiator is advantageously not more than 0.2 times the molar amount of the sulfonyl chloride, preferably not more than 0.1 times, the optimum zone being between 1% and 8% of the amount of sulfonyl chloride. The reaction is advantageously conducted such that the release of the free radicals takes place gradually. A good technique for achieving this objective consists in adding the initiator, i.e. the free-radical generator, slowly and gradually. Another technique consists in using a temperature that allows the release of the free radicals to be controlled.

The reaction temperature is regulated such that it is between ambient temperature and 150° C., preferably between 50 and 120° C. and more preferentially between 60 and 100° C.

It should be noted that, for certain substrates, the reaction does not need an initiator, especially for substrates whose double bond bears a chalcogen, usually an oxygen. However, the use of a free-radical generator still improves the reaction yield.

The amount of substrate relative to the sulfonyl chloride is about once the molar amount. However, to satisfy specific problems, it is possible to depart considerably from this value which corresponds to the stoichiometric value as defined by the following reaction:

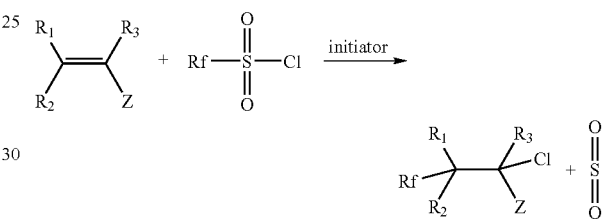

In particular, when there is a large risk of polymerization, a smaller amount of compounds bearing a double bond may be used relative to the amount of sulfonyl chloride. Thus, it is possible to vary very widely the ratio between the substrate bearing the double bond and the sulfonyl chloride. However, in the majority of cases, the ratio is of the order of 1±0.5.

The pressure may vary within large proportions but it is preferable to work at an autogenous pressure or at atmospheric pressure.

Although its presence is not necessary, it is possible to use a solvent. The solvents that may be used are solvents that are inert toward sulfonyl chloride and that do not constitute free-radical traps.

Mention may thus be made of the hydrocarbons and halogenated derivatives that are usually used in free-radical chlorination reactions.

More specifically, alkanes with a suitable boiling point, i.e. whose boiling point is at least equal to the temperature at which it is desired to work; petroleum fractions; aromatic chloro derivatives, are all entirely acceptable.

The sulfonyl chlorides that are preferred are those corresponding to the formula $R_f$—$SO_2$—Cl in which $R_f$ corresponds to formula (IV):

$$EWG-(CX_2)_p-$$

in which:
the radicals X, which may be similar (i.e. they are identical) or different, represent a chlorine, a fluorine or a radical of formula 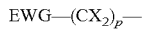 $C_nF_{2n+1}$ with n being an integer not more than 5 and preferably not more than 2, with the condition that at least one of the radicals X is fluorine; when p is equal to 1, EWG is an electron-withdrawing group (that is to say that the Hammett constant sigma p is >0, advantageously at least equal to 0.2), otherwise it may be any radical, which is preferably inert, and advantageously an electron-withdrawing group (cf. preceding lines);

p is a positive integer, i.e. it cannot comprise the value 0.

EWG is advantageously fluorine, especially when p is less than or equal to 2.

The radicals X are advantageously all fluorine, especially when p is less than or equal to 2.

Another value of EWG (electron-withdrawing group) is when it equals chlorine; in this case, EWG is a chlorine.

p represents an integer advantageously not more than 4 and preferably not more than 2;

EWG advantageously represents an electron-withdrawing group whose optional functions are inert under the reaction conditions, advantageously fluorine or a perfluoro residue of formula $C_nF_{2n+1}$, with n being an integer not more than 8 and advantageously not more than 5.

The total carbon number of Rf is advantageously between 1 and 15 and preferably between 1 and 10.

It is advantageous that Rf should be of formula $C_rF_{2r+1}$ with r being an integer not more than 15 and advantageously between 1 and 10.

The present invention is particularly advantageous for radicals $R_f$ of low molecular weight, i.e. those that are relatively volatile (with a boiling point at atmospheric pressure of not more than 100° C.). The technique is particularly advantageous for radicals $R_f$ containing a radical with an odd number of carbons, and particular mention should be made for radicals $R_f$ of $C_1$, $C_2$ and $C_3$.

Radicals $R_f$ higher than $C_6$ are less advantageous.

The compounds that give the most advantageous results are those in which Z is of structure $Y-R_4$ with Y being a chalcogen, preferably a light chalcogen, i.e. sulfur or oxygen and more particularly the latter.

$R_4$ is a hydrocarbyl group, i.e. a group containing hydrogen and carbon. These hydrocarbyl groups may be alkyl (i.e. an alcohol residue of which the hydroxyl function is ignored), an aryl or an oxygenated acid residue (i.e. a residue whose acidic hydrogen is borne by an oxygen) from which an OH function has been removed. In this latter group, mention may be made of acyls, phosphoryls, phosphonyls, phosphinyls and sulfonyls. The acids $R_4Y(O)_q$— advantageously have a pKa of not more than 10, preferably not more than 8 and more preferentially not more than 6. Acids with a Hammett constant that is greater than or equal to that of perfluoroalkane-sulfonic acids, and especially triflic acid, are not preferred.

The group $R_4$ is advantageously an electron-withdrawing group of the acyl type.

It is preferable for the molecule bearing the double bond not to contain a strongly reductive function, or a nucleophilic function capable of reacting with the sulfonyl chloride.

The total carbon number of the substrate of formula I is generally not more than 50 (one significant figure) and better still not more than 30. In particular, when Rf is of the type $CX_3 (CX_2)_s$, the presence of halogens heavier than fluorine at the other end of the chain Rf liable to give spurious reactions, especially when the chain Rf is short (s less than or equal to 5 and, even, less than or equal to 4). As has been stated previously, another aim of the present invention is that of providing reaction intermediates that allow novel routes of access.

This aim is achieved by means of compounds corresponding to the formula:

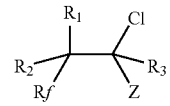

with $R_1$, $R_2$, Z and Rf being chosen from the same values (and with the same preferences) as above, but with the following additional conditions:

with $R_1$ and $R_2$ chosen from hydrogen and hydrocarbyl radicals, with the condition that one of the radicals $R_1$ or $R_2$ at least is equal to H, and advantageously both of them;

with Z chosen from radicals of formula $(CHR')_m-Y-R_4$ in which $R_4-Y$ is such that $R_4YH$ is an oxygenated acid, the possible aromatic nucleus (nuclei) being separated from said double bond by at least two atoms of $sp^3$ hybridization (in the case of Z, an oxygen atom and at least one carbon atom, advantageously at least two $sp^3$ carbon atoms; in the other cases, at least two $sp^3$ carbon atoms);

the total carbon number of the molecule being at least equal to (6−m) and not more than 30, and advantageously in which:

❖ Y is a chalcogen, advantageously a light chalcogen, preferably oxygen;

❖ R' represents a hydrocarbyl, advantageously of not more than four carbons, or preferably a hydrogen;

❖ m is equal to 1 or, preferably, to zero;

❖ and $R_4$ is chosen from hydrocarbyl groups, advantageously from acyls.

It is advantageous for Rf to be of formula $C_rF_{2r+1}$ with r being an integer not more than 15, advantageously between 1 and 10 and preferably not more than 4.

For steric reasons, it is preferable for said acid $R_4-YH$ not to comprise any branching alpha or beta to the atom bearing the acidic proton, in general oxygen; thus, for example, in the case of a carboxylic acid, the atom bearing the carboxylic function, which is beta to the oxygen bearing the proton, is advantageously neither tertiary nor even secondary, nor does it correspond to the branching of an aromatic nucleus.

One subfamily of the above compounds is particularly novel, namely the family in which m is equal to zero; when $R_3$ is other than H, the compounds are highly reactive [lacuna] constitutes only reaction intermediates but remains identifiable, especially at low temperature by fluorine-19 NMR. When $R_3$ is hydrogen, these compounds are surprisingly stable. These two subfamilies decompose or are hydrolyzed to carbonyl, aldehyde or ketone derivatives, see the examples. This subfamily may thus be used to synthesize by hydrolysis, for example acid hydrolysis, aldehydes or ketones and derivatives thereof. A subsequent oxidation, which is known per se, of the aldehydes gives the corresponding acids.

Another advantageous subfamily lies in the alcohol and the corresponding esters in which m is equal to one and Y is oxygen and in which, advantageously, $R_3$ is H.

The alcohol is readily synthesized by alcoholysis of the corresponding ester, without touching the chlorine borne by the carbon atom adjacent to that bearing the ester function and then the alcohol:

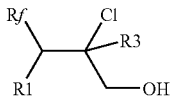

The alcohol or ester readily lead, especially under the action of strong base (sodium hydroxide, potassium hydroxide or quaternary ammonium hydroxide), the associated acid of which has a pKa at least equal to 12 and advantageously to 13, to epoxides:

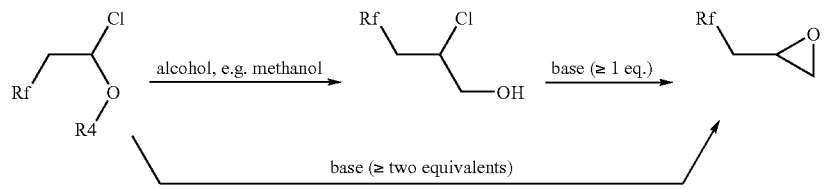

See the examples below.

The epoxides $Rf\text{-}CHR_1CR'(O)CH_2$ are important organic intermediates given the importance of "perfluoroalkylpropylene oxides and related compounds" in application on account of their common properties:

polymerization catalysts, urethane-fluoropolyether acrylate copolymers, treatment of metal surfaces, transparent materials, hydrophobic coatings, cosmetics.

As has been stated previously, for reasons of ease of synthesis according to the invention and for reasons of stability, it is desirable for Rf not to bear in the omega position (i.e. at the other end of the chain) of the longest chain, a halogen heavier than fluorine (i.e. chlorine, bromine or iodine).

The nonlimiting examples that follow illustrate the invention.

EXAMPLE 1 COMPARATIVE

Action of trifluoromethanesulfonyl chloride on enol ethers and esters in the presence of ruthenium activated with triphenylphosphine (for the operating conditions, see Kamigata et al., J. Chem. Soc. Perkin Trans., 1991, page 631, left-hand column).

| Substrate | θ° C. | T(h) | DC %[b][1] | DC %[a] | RY %[b] | Comments |
|---|---|---|---|---|---|---|
| OEt / OEt (4) | 100° C. | 24.5 | 100 | nd[c] | 0 | Formation with RY = 91.5% $CF_3SO_2Et$ (characterization by $^{19}F$ NMR and GC/MS). |
| | | | | | | Detection by GC/MS of byproducts derived from (4): $-ClCH_2CH_2CO_2Et$ $-CH_3CO_2Et$ |
| $COOC_9H_{19}$ / H (5) | 100° C. | 17.5 | 40 | 68 | 0 | Detection by GC/MS analysis of many decomposition products of $CH_2=CHOCOC_9H_{19}$: |
| | 120° C. | 16 | 38 | 87.5 | 0 | E.g.: $C_9H_{19}CO_2H$ |
| $OC_{12}H_{25}$ / H (6) | 100° C. | 16 | 49 | 100 | 0 | Detection by GC/MS analysis of many decomposition products of $CH_2=COOC_{12}H_{25}$: $-C_{12}H_{25}OH$ (majority) $-C_{11}H_{23}CHO$ $-C_{11}H_{23}COCF_3$ |

[a] GC assay with internal standard
[b] $^{19}F$ NMR assay with internal standard
[c] not determined (&)
[1] relative to the sulfonyl chloride

EXAMPLE 2

Action on Various Vinyl Ethers

The initiator (0.376 mmol), the alkene (9.4 mmol) then triflyl chloride (9.4 mmol) are successively introduced into a 60 mm Schott tube at 20° C. The reaction is that indicated in the general equation of the description with $R_1$, $R_2$, $R_3$=H.

| Test (a) | Sub-strate | R | Initiator | t (h) | Sub-strate | DC %[b] | RY %[b] |
|---|---|---|---|---|---|---|---|
| RON 240B | 5 | $OCOC_9H_{19}$ | $(PhCO_2)_2$ | 13.5 | 1/1 | 82 | 41 |
| BJ 540A | | $OCOC_9H_{19}$ | $(PhCO_2)_2$ | 7 | 1/1 | 77 | 45 |
| BJ 544B | | $OCOC_9H_{19}$ | AIBN | 17 | 1/1.2 | 76.5 | 50 |
| BJ 545A | | $OCOC_9H_{19}$ | AIBN | 7 | 1/1.2 | 75.5 | 50 |
| BOA 137 | (12) | $OCOCH_3$ | AIBN | 7 | 1/1 | 82 | 52.5 |
| BOA 9 | (13) | $[(CH_2)_7CH_3]$ | AIBN | 7 | 1/1.1 | 91 | 77.5 |

The addition products were identified by fluorine-19 NMR and by gas chromatography coupled to a mass spectrograph.

The reaction was performed at 90° C. and, at this temperature, the reaction is complete, or at the very least has ended, after 7 hours.

Contrary to the rutheniumtriphenylphosphine chloride system, free-radical initiators allow the addition of trifluoromethyl, on the one hand, and of chloride, on the other hand, to the double bond of enol esters.

EXAMPLE 3

Study of the Role of the Amount of Free-Radical Initiators

One equivalent of triflyl chloride, AIBN in variable proportions and 1.2 equivalents of vinyl laurate are successively introduced into a 60-ml Schott tube, the reaction mixture is then maintained at 90° C. for 7 hours while the solution is stirred on a heating block.

The crude reaction mixture is analyzed by gas chromatography and fluorine-19 NMR.

| Mol % initiator | DC %[b] | DC %[c] | RY %[b] |
|---|---|---|---|
| 0 | 70 | 57 | 25 |
| 1 | 77.2 | — | 43 |
| 4 | 84 | 86.5 | 56 |
| 6 | 85 | 95 | 54 |

EXAMPLE 4 COMPARATIVE

Influence of the Nature of the triflyl halide, Reaction with perfluorobutanesulfonic fluorides Under conditions similar to the previous test, perfluorobutanesulfonic fluoride is tested in place of the triflyl chloride.

| Substrate | R | DC %[b] | DC %[c] | RY %[b] |
|---|---|---|---|---|
| (12) | —OAc | 27 | 79.5 | 0 |

Although the alkene reacts, the desired product is not obtained.

EXAMPLE 5 COMPARATIVE

In the Case of Styrene

The above operating conditions were repeated, using styrene as the vinyl substrate. The results are collated in the table below.

| Test | DC %[a] | DC %[a] | Comments |
|---|---|---|---|
| BOA 1 | 65 | 10 | By $^{19}F$ NMR and GC/MS the formation of the "dimer" is detected (2 diastereoisomers) |

Oligomerization or polymerization products are mainly formed.

EXAMPLE 6

Comparison Between Vinyl Ethers and Vinyl Esters

The above operating conditions were carried out on various substrates using triflyl chloride. The substrates used have different values of Z.

| Test | Z | DC %[a] | RY %[a] |
|---|---|---|---|
| BJ 542B | $OC_{12}H_{25}$ | 68 | 23.5 |
| BOA 142 | SPh | 91 | 22.5 |
| BOA 137 | OAc | 82 | 52.5 |
| RON 274 | $OCOC_{11}H_{23}$ | 85 | 54 |

EXAMPLE 7

Unfavorable Role of the Phenyl Radical

The above conditions were used on various substrates, with the value of Z being varied. The results are collated in the table below. The ketone corresponds to the desired product after elimination of an acyl chloride.

| Substrate | DC %[a] | RY %[a] | Formation of ketone |
|---|---|---|---|
| $CH_2=CH-OAc$ | 82 | 52.5 | — |
| $CH_2=C(CH_3)-OAc$ | 78.5 | 0 | 50 |
| $CH_2=C(Ph)-OAc$ | 69 | 1.5 | 5 |
| $CH_2=C(CH_3)-OSiMe_3$ | 89 | 0 | 28 |
| $CH_2=C(Ph)-OSiMe_3$ | 57.5 | 0 | 9 |

EXAMPLE 8
Experimental Section

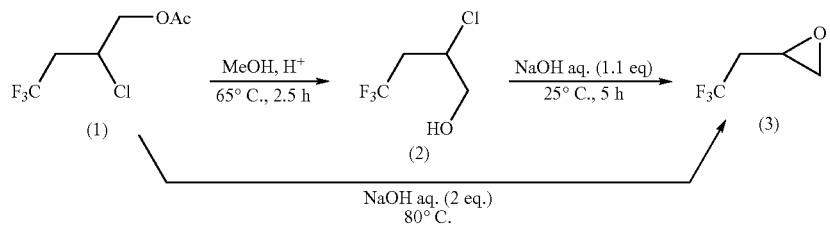

The acyl herein is such that Ac—O— is a propionate

Synthesis starting with 2-chloro-4,4,4-trifluorobutyl propionate (1)

15% sodium hydroxide (107 mmol) and 2-chloro-4,4,4-trifluorobutyl propionate (1) (10.03 g, 49.0 mmol) are loaded into a perfectly stirred and standardized 100-ml reactor equipped with a condenser and a thermometer. The reactor is placed in an oil bath at 90° C. with stirring at 320 rpm. The temperature of the medium reaches 84° C. After 24 minutes, the system is cooled with a bath of cardice. The medium is two-phase and the lower phase is colorless. GC allows the partial state of progress of the reaction to be monitored. The reactor is placed at 90° C. for 30 minutes at 520 rpm. The temperature of the medium reaches 84° C. The system is cooled in a bath of cardice. Monitoring by GC indicates the end of the reaction. The medium is two-phase and yellow. The lower phase is separated out by settling. 4.11 g ($RY_{assayed}$=46%) are recovered. In the same manner, a second batch is carried out (30 minutes with stirring at 520 rpm). 4.43 g ($RY_{assayed}$=43%) are recovered. The organic phases are distilled off under atmospheric pressure simply with a column head ($t_{passage}$=68-83° C.). 4.83 g of a colorless liquid are recovered ($P_{mass}$=96%).

Synthesis from the Alcohol (2)

2-Chloro-4,4,4-trifluorobutan-1-ol (2)

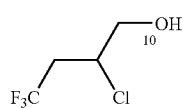

2-Chloro-4,4,4-trifluorobutyl propionate (1) (9.58 g, 95.8 mmol), methanol (92 ml, 2.3 mol) and concentrated sulfuric acid (0.53 g, 10 mmol) are loaded into a 250-ml three-necked flask equipped with a condenser, a thermometer, a septum and a magnetic stirrer. The reaction medium is heated to reflux (between 60 and 65° C.). The mixture is left stirring for 2.5 hours. Distillation is performed at atmospheric pressure to remove the methanol and the methyl acetate. The residue is distilled at reduced pressure (38 mmHg).

The following are collected:
   1st between 38 and 58° C.: 0.318 g at more than 99% pure
   2nd between 60 and 66° C.: 10.15 g at more than 99% pure
   3rd between 57 and 35° C.: 0.63 g at more than 95% pure.

11.1 g are thus finally collected. Assay by 19F NMR gives a $RY_{isolated}$ (2)=69%.

b.p.=60-65° C./38 mmHg

4,4,4-Trifluoro-1,2-epoxybutane (3)

15% sodium hydroxide (37 mmol) and 2-chloro-4,4,4-trifluorobutan-1-ol (2) are loaded into a perfectly stirred and standardized 100-ml reactor equipped with a condenser and a thermometer. The mixture is stirred at 20° C. for 1 hour 40 minutes at 250 rpm. A two-phase medium is obtained. GC of the mixture indicates a virtually complete DC. The mixture is allowed to settle for 2 hours. The two phases are separated. The organic phase is washed with 5 ml of $H_2O$. 3.1 g of crude product are recovered. $^{19}F$ NMR analysis gives an $RY_{assayed}$ (3)=68% b.p.=68-69° C./627 mmHg

EXAMPLE 9

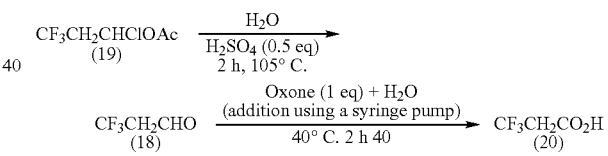

3,3,3-Trifluoropropanal (18)

1-Chloro-3,3,3-trifluoropropyl acetate (19) (10.02 g, 52.7 mmol), water (51 ml) and 95% sulfuric acid (1.5 ml, 26.6 mmol) are loaded into a 100-ml four-necked flask equipped with a magnetic stirrer, a cardice trap (connected to an antireturn bubbler) and a thermometer. The mixture is heated to 105° C. When the temperature of the medium reaches 87.5° C., a reflux appears. The temperature falls by a few degrees (83° C.). The mixture is heated for 2 hours. It is then cooled to ambient temperature and the trap is kept. The acetone in the trap is replaced with warm water. The trap is washed with water and the washing liquors are combined with the reaction medium. Assay by $^{19}F$ NMR gives an $RY_{assayed}$ (18) of 89%. The 3,3,3-trifluoropropanal (18) is stored in the acidic aqueous medium.

3,3,3-Trifluoropropionic acid (20)

1-Chloro-3,3,3-trifluoropropyl acetate (19) (1.0 g, 5.3 mmol), water (5 ml) and 95% sulfuric acid (0.15 ml, 2.6 mmol) are loaded into a 50-ml three-necked flask equipped with a magnetic stirrer, a cardice trap (connected to an antireturn bubbler), a thermometer and a Teflon tube. The mixture is heated to 105° C. When the temperature of the medium reaches 92° C., a reflux appears. The temperature falls by a few degrees (87° C.). The mixture is heated for 2 hours. It is then allowed to cool to ambient temperature, and the trap is kept. The acetone in the trap is replaced with warm water. The trap is washed with a minimum amount of water. Assay by $^{19}$F NMR gives an $RY_{assayed}$ (20) of 73% (3.88 mmol). The solution of Oxone® (2.25 g, 3.67 mmol) in 10 ml of water is prepared. This solution is added by syringe pump over 30 minutes at 40° C. The mixture is left at 40° C. for 2 hours 15 minutes. 2.07 mmol of acid are obtained with an $RY_{oxidation}$ (20)=73%.

EXAMPLE 10 the fact that there is now a tertiary carbon instead of a secondary carbon—as in $CF_3CH_2CHClOAc$—this reaction brings about a predominant elimination of acetyl chloride:

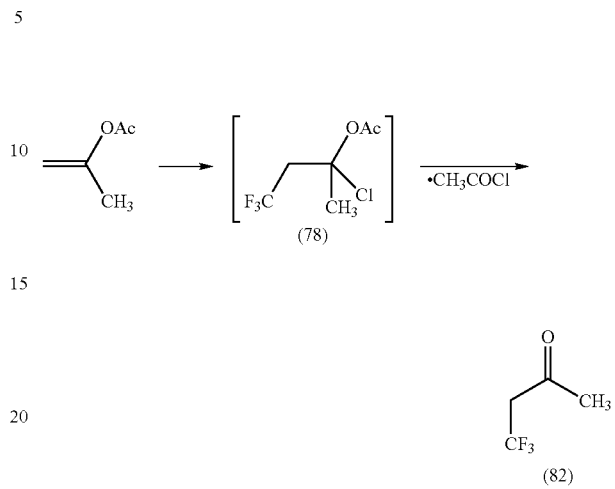

As shown by the results below, the intermediate (78) was detected by working at lower temperature and by analyzing the reaction medium after reaction for 1 to 3 hours:

relative to:

Heat-stable (Isolated by Isolation)

The presence of a $CH_3$ unit is not an inconvenience for the trifluoromethylation reaction. However, the product of vicinal-chlorotrifluoro-methylation is not isolated; as a result of

| Test | (1)/(74) | θ° C. | t (h) | DC % (1) %[b] | DC % (74) %[a] | RY (78) %[b] | RY (82) %[b] |
|---|---|---|---|---|---|---|---|
| BJ665 | 1/1 | 80 | 1 | 60 | 65 | 28.5 | 7.5 |
|  |  |  | 2 | 68 | 75.5 | 21 | 19 |
| BJ666 | 1/1 | 90 | 1 | 69 | 78 | 20 | 23 |
|  |  |  | 2 | 72 | 90 | 5 | 39 |
|  |  |  | 3 | 76 | >95 | 1 | 39.5 |

[a]GC assay with internal standard,

[b]assay by $^{19}$F NNR with internal standard: (78): δ = 7.84 ppm (/TFA) and (82): δ = 8.97 ppm (/TFA).

The invention claimed is:

1. A process for functionalizing a double bond corresponding to the following formula I:

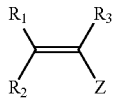

wherein:
$R_1$, $R_2$ and $R_3$, are hydrogen atoms attached to said double bond via an sp³ carbon, wherein:
Z is $CH_2$—O—$R_4$, where
$R_4$ is a hydrocarbyl or silyl group,
said process comprising the step reacting without polymerizing said double bond with a sulfonyl chloride compound perhalogenated on a sulfur-bearing carbon of the sulfonyl function, in the presence of a free-radical initiator, wherein the free-radical initiator is an initiator by homolytic cleavage.

2. The process according to claim 1, wherein $R_4$ is an electron-withdrawing group.

3. The process according to claim 1, wherein the perhalogenated sulfonyl chloride has the formula $R_f$—$SO_2$—Cl, wherein $R_f$ has the formula EWG—$(CX_2)_p$—, wherein:

X groups, which are similar or different, represent a chlorine atom, a fluorine atom or a group of formula $C_nF_{2n+1}$ wherein n is an integer of not more than 5, with the condition that at least one of the X groups is fluorine,
p is integer of not more than 2,
EWG is an electron-withdrawing group, optionally comprising functions, said functions being inert under the reaction conditions, and
the total number of carbon atoms in $R_f$ is of between 1 and 15.

4. The process according to claim 3, wherein:
X groups, which are similar or different, represent a chlorine atom, a fluorine atom or a group of formula $C_nF_{2n+1}$ wherein n is an integer of not more than 2, with the condition that at least one of the X groups is fluorine, EWG is an electron-withdrawing group, comprising inert functions under the reaction conditions, said functions being a fluorine atom or a perfluoro residue of formula $C_nF_{2n+1}$, with n being an integer of not more than 8,
the total number of carbon in $R_f$ is of between 1 and 10.

5. The process according to claim 3, wherein $R_f$ contains not more than 6 carbon atoms.

6. The process according to claim 5, wherein $R_f$ contains not more than 3 carbon atoms.

7. The process according to claim 1, wherein $R_4$ is an acyl group comprising not more than 15 carbon atoms.

8. The process according to claim 7, wherein the acyl group comprises not more than 10 carbon atoms.

* * * * *